(12) United States Patent
Luo et al.

(10) Patent No.: US 11,333,590 B1
(45) Date of Patent: May 17, 2022

(54) EXPERIMENTAL SYSTEM FOR SIMULATING CREEP AND STICK-SLIP DISLOCATIONS OF FAULT IN TUNNEL STRUCTURE

(71) Applicant: INSTITUTE OF GEOLOGY AND GEOPHYSICS, CHINESE ACADEMY OF SCIENCES, Beijing (CN)

(72) Inventors: Guangming Luo, Beijing (CN); Shengwen Qi, Beijing (CN); Bowen Zheng, Beijing (CN); Yu Zou, Beijing (CN); Manchao He, Beijing (CN); Hui Zhou, Beijing (CN); Xiaolin Huang, Beijing (CN); Songfeng Guo, Beijing (CN); Ning Liang, Beijing (CN)

(73) Assignee: INSTITUTE OF GEOLOGY AND GEOPHYSICS, CHINESE ACADEMY OF SCIENCES, Beijing (CN)

( * ) Notice: Subject to any disclaimer, the term of this patent is extended or adjusted under 35 U.S.C. 154(b) by 0 days.

(21) Appl. No.: 17/588,216

(22) Filed: Jan. 29, 2022

(30) Foreign Application Priority Data

Jul. 21, 2021 (CN) .......................... 202110822363.3

(51) Int. Cl.
*G01N 3/00* (2006.01)
*G01N 3/08* (2006.01)
(Continued)

(52) U.S. Cl.
CPC .............. *G01N 3/08* (2013.01); *G01N 33/24* (2013.01); *G09B 23/40* (2013.01); *G01N 2203/0067* (2013.01)

(58) Field of Classification Search
CPC .. G01N 3/08; G01N 33/24; G01N 2203/0067; G09B 23/40
See application file for complete search history.

(56) References Cited

U.S. PATENT DOCUMENTS

| 11,048,002 | B1* | 6/2021 | Mao | ........................ G06T 17/05 |
| 2009/0006050 | A1* | 1/2009 | Chen | ........................ G06F 30/33 |
|  |  |  |  | 703/4 |

(Continued)

FOREIGN PATENT DOCUMENTS

| CN | 106875804 A | 6/2017 |
| CN | 107271128 A | 10/2017 |

(Continued)

*Primary Examiner* — Max H Noori
(74) *Attorney, Agent, or Firm* — Bayramoglu Law Offices LLC (57) ABSTRACT

An experimental system for simulating creep and stick-slip dislocations of a fault in a tunnel structure includes a box structure, a supporting device and a fault dislocation loading system. A friction effect layer, a first surrounding rock layer, a tunnel structure model, a second surrounding rock layer and an overburden pressure layer are sequentially arranged in the box structure from bottom to top. The bottom of the box structure is provided with a through hole. A plate assembly is provided on the through hole, and includes a first guide plate, a second guide plate and a loading plate. Inner sides of the first guide plate and the second guide plate are respectively provided with a first slide rail and a second slide rail. The loading plate moves along the first slide rail and the second slide rail under the action of the fault dislocation loading system.

14 Claims, 2 Drawing Sheets

(51) Int. Cl.
*G01N 33/24* (2006.01)
*G09B 23/40* (2006.01)

(56) References Cited

U.S. PATENT DOCUMENTS

| | | | | |
|---|---|---|---|---|
| 2010/0204972 | A1* | 8/2010 | Hsu | G01V 11/00 |
| | | | | 703/10 |
| 2011/0170373 | A1* | 7/2011 | Hsu | G01V 1/282 |
| | | | | 367/73 |
| 2014/0288898 | A1* | 9/2014 | Fukuda | G06F 30/367 |
| | | | | 703/2 |
| 2019/0325331 | A1* | 10/2019 | Benhallam | E21B 41/00 |
| 2021/0049933 | A1 | 2/2021 | Chen et al. | |
| 2021/0049934 | A1 | 2/2021 | Chen et al. | |
| 2022/0010680 | A1* | 1/2022 | Wang | E21D 11/15 |

FOREIGN PATENT DOCUMENTS

| | | |
|---|---|---|
| CN | 108548712 A | 9/2018 |
| CN | 108982219 A | 12/2018 |
| CN | 111081110 A | 4/2020 |
| CN | 112362479 A | 2/2021 |

\* cited by examiner

EXPERIMENTAL SYSTEM FOR SIMULATING CREEP AND STICK-SLIP DISLOCATIONS OF FAULT IN TUNNEL STRUCTURE

CROSS REFERENCE TO THE RELATED APPLICATIONS

This application is based upon and claims priority to Chinese Patent Application No. 202110822363.3, filed on Jul. 21, 2021, the entire contents of which are incorporated herein by reference.

TECHNICAL FIELD

The present invention belongs to the technical field of geomechanics experiments of rock mass engineering, and more particularly relates to an experimental system for simulating creep and stick-slip dislocations of a fault in a tunnel structure.

BACKGROUND

At present, China's central and western regions are vigorously developing infrastructures such as railways and highways. However, in these regions, the construction of cross-fault tunnels is facing stability problems due to the complex structures and frequent earthquakes. Therefore, it is urgent to deeply study the influences of fault dislocations on tunnel engineering. There are two types of fault dislocations, i.e., creep and stick-slip. The existing research mainly uses model boxes for physical simulation, which can only achieve creep or stick-slip alone. Meanwhile, the dislocation effect is implemented by a loading device directly acting on surrounding rock-similar material, without reflecting the effect of the relative motion of the two rock layers of the fault transferred to the overlying surrounding rock.

SUMMARY

In order to solve the problem of poor reliability of data acquired by the existing experimental device in the prior art, the present invention provides an experimental system for simulating creep and stick-slip dislocations of a fault in a tunnel structure. The experimental system for simulating creep and stick-slip dislocations of a fault in a tunnel structure includes a model box system and a fault dislocation loading system, where the fault dislocation loading system is provided under the model box system;

the model box system includes a hollow box structure and a supporting device provided under the box structure; a friction effect layer, a first surrounding rock layer, a tunnel structure model, a second surrounding rock layer and an overburden pressure layer are sequentially arranged in the box structure from bottom to top; a bottom of the box structure is provided with a through hole; and a plate assembly is provided on the through hole to close the bottom of the box structure;

the plate assembly includes a loading plate, a first guide plate and a second guide plate; the loading plate covers the through hole; the first guide plate and the second guide plate are arranged on two sides of the loading plate and are connected to a bottom plate of the box structure; a side of the first guide plate adjacent to the second guide plate is provided with a first slide rail; a side of the second guide plate adjacent to the first guide plate is provided with a second slide rail; and the two sides of the loading plate are slidably provided on the first slide rail and the second slide rail; and the fault dislocation loading system is provided under the loading plate; the loading plate moves along the first slide rail and the second slide rail under the action of the fault dislocation loading system; and the friction effect layer provides fault dislocation power to the tunnel structure model through the first surrounding rock layer under the action of the loading plate.

In some preferred embodiments, the first guide plate and the second guide plate may be inclined plates; two side end surfaces of the loading plate may be inclined surfaces; and the first guide plate and the second guide plate may be arranged in parallel with the two side end surfaces of the loading plate;

a third slide rail may be provided at a bottom of the loading plate; and the fault dislocation loading system may include a plurality of hydraulic power devices; tops of the plurality of hydraulic power devices abut against the third slide rail during an experiment, and tops of the plurality of hydraulic power devices may be slidable on the third slide rail.

In some preferred embodiments, the friction effect layer may include clay mineral and quartz sand; each of the first surrounding rock layer and the second surrounding rock layer may be a mixture of quartz sand, barite powder, gypsum and water; and the tunnel structure model may be provided between the first surrounding rock layer and the second surrounding rock layer.

In some preferred embodiments, a weight ratio of the clay mineral to the quartz sand may be 1:1; and the clay mineral may be montmorillonite, and the quartz sand may be 80-mesh ordinary quartz sand.

In some preferred embodiments, the weight ratio of the clay mineral to the quartz sand may be 1:9; and the clay mineral may be kaolinite, and the quartz sand may be 40-mesh ordinary quartz sand.

In some preferred embodiments, a height of the first guide plate and a height of the second guide plate may be less than a height of the friction effect layer; and an angle between the first guide plate and the bottom plate of the box structure may be θ, where $\theta \in [15°, 90°]$.

In some preferred embodiments, the height of the friction effect layer may be h, and a height of the box structure may be H, $h \in [\frac{1}{3}H, \frac{1}{2}H]$.

In some preferred embodiments, the overburden pressure layer may be an iron sand layer;

the supporting device may include a plurality of supporting frames, and the plurality of supporting frames may be arranged in an array; and the supporting frame may have a T-shaped structure, and the top of the T-shaped structure may be detachably connected to the bottom of the box structure.

In some preferred embodiments, the bottom plate of the box structure may include a first region and a second region, and the first region and the second region may be symmetrically arranged; the through hole may be provided at the first region or the second region; and a front panel, a rear panel, a left panel and a right panel of the box structure may be made of organic glass.

In some preferred embodiments, the experimental system may further include a master control center, a deformation detection device and a high-energy accelerator-based computed tomography (CT) scanning system; and the deformation detection device and the high-energy accelerator-based CT scanning system may be connected to the master control center through signals;

the deformation detection device may include a first deformation detection assembly, a second deformation detection assembly, a third deformation detection assembly and a fourth deformation detection assembly; and the first deformation detection assembly may be provided in the friction effect layer to detect deformation of the friction effect layer in real time;

the second deformation detection assembly may be provided in the first surrounding rock layer to detect deformation of the first surrounding rock layer in real time;

the third deformation detection assembly may be provided in the tunnel structure model to detect deformation of a peripheral side wall of the tunnel structure model in real time;

the fourth deformation detection assembly may be provided in the second surrounding rock layer to detect deformation of the second surrounding rock layer in real time; and the high-energy accelerator-based CT scanning system may include a ray source device and a detector; and the ray source device and the detector may be respectively arranged on two sides of the tunnel structure model in the box structure for real-time detection of stress and deformation states of the rock surrounding the tunnel structure model and a tunnel structure.

1) Based on the influences of the proportion of the clay mineral in the friction effect layer made of materials similar to the surrounding rock on the friction stability, the present invention simulates the influences of creep and stick-slip of the fault on the tunnel structure through the same device. The simulation only needs to change the ratio of the clay mineral to the quartz sand in the friction layer, which is operable and low-cost. It is helpful to promote the stability research of cross-fault tunnel engineering, and has important reference significance for the construction of cross-fault tunnel engineering.

2) In the present invention, the materials similar to the surrounding rock are laid in layers. The friction effect layer is used to simulate the dislocation of the faulted rock and transfer the dislocation to the overlying surrounding rock, the surrounding rock layer is used to simulate the surrounding rock environment where a tunnel is located, and the iron sand layer is used to simulate the stress from the overburden pressure. Compared with the similar material laying method in the prior art, the present invention improves the restoration to the real environment, improves the credibility of the experimental results, and is more scientific and reasonable.

3) The present invention replaces expensive hydraulic servo power sources with hydraulic jacks to achieve the two types of dislocation effects, greatly reducing the cost of the experiment.

4) The present invention has a simple structure and easy assembly, which facilitates a large number of experiments, and improves the efficiency of experiments and the credibility of results.

BRIEF DESCRIPTION OF THE DRAWINGS

Other features, objectives and advantages of the present application will become more apparent upon reading the detailed description of the non-restrictive embodiments with reference to the following drawings.

Reference Numerals: 110. box structure; 120. supporting device; 131. loading plate; 132. first guide plate; 133. second guide plate; 134. first slide rail; 135. second slide rail; 136. third slide rail; 200. fault dislocation loading system; 310. friction effect layer; 320. first surrounding rock layer; 330. tunnel structure model; 340. second surrounding rock layer; and 350. overburden pressure layer.

DETAILED DESCRIPTION OF THE EMBODIMENTS

The preferred implementations of the present invention are described below with reference to the drawings. Those skilled in the art should understand that the implementations herein are merely intended to explain the technical principles of the present invention, rather than to limit the protection scope of the present invention.

The present invention provides an experimental system for simulating creep and stick-slip dislocations of a fault in a tunnel structure. The experimental system includes a model box system and a fault dislocation loading system. The fault dislocation loading system is provided under the model box system. The model box system includes a hollow box structure and a supporting device provided under the box structure. A friction effect layer, a first surrounding rock layer, a tunnel structure model, a second surrounding rock layer and an overburden pressure layer are sequentially arranged in the box structure from bottom to top. A bottom of the box structure is provided with a through hole. A plate assembly is provided on the through hole to close the bottom of the box structure. The plate assembly includes a loading plate, a first guide plate and a second guide plate. The loading plate covers the through hole. The first guide plate and the second guide plate are arranged on two sides of the loading plate and are connected to a bottom plate of the box structure. A side of the first guide plate adjacent to the second guide plate is provided with a first slide rail; a side of the second guide plate adjacent to the first guide plate is provided with a second slide rail. The two sides of the loading plate are slidably provided on the first slide rail and the second slide rail. The fault dislocation loading system is provided under the loading plate. The loading plate moves along the first slide rail and the second slide rail under the action of the fault dislocation loading system. The friction effect layer provides fault dislocation power to the tunnel structure model through the first surrounding rock layer under the action of the loading plate.

The experimental system of the present invention performs physical simulation on the influences of creep and stick-slip dislocations of a fault on a tunnel structure through the same experimental equipment. The present invention only needs to change the ratio of materials similar to the surrounding rock, and changes the dislocations between creep and stick-slip by adjusting the ratio of the materials on the friction stability, so as to study the influence of different fault dislocations on tunnel engineering. In the present invention, the friction effect layer produces the creep and stick-slip dislocation effects desired by the experiment, and the first surrounding rock layer transfers the fault dislocation power to the tunnel structure model. This is helpful to promote the stability research of cross-fault tunnel engineering, and has important reference significance for the construction of cross-fault tunnel engineering.

The present invention is described in further detail below with reference to the drawings and embodiments.

Figure 1:
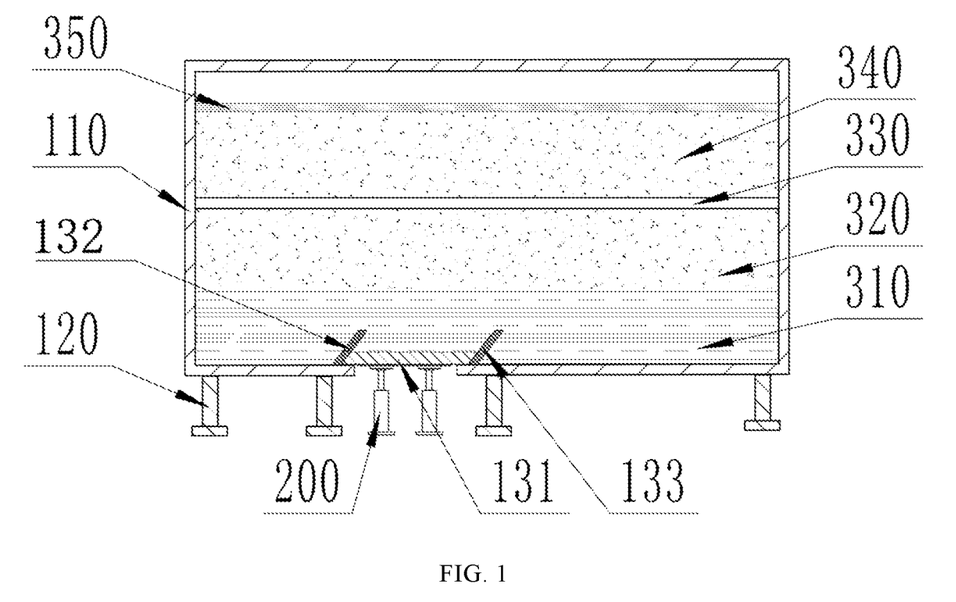
FIG. 1 is a sectional view according to a specific embodiment of the present invention.
Figure 2:
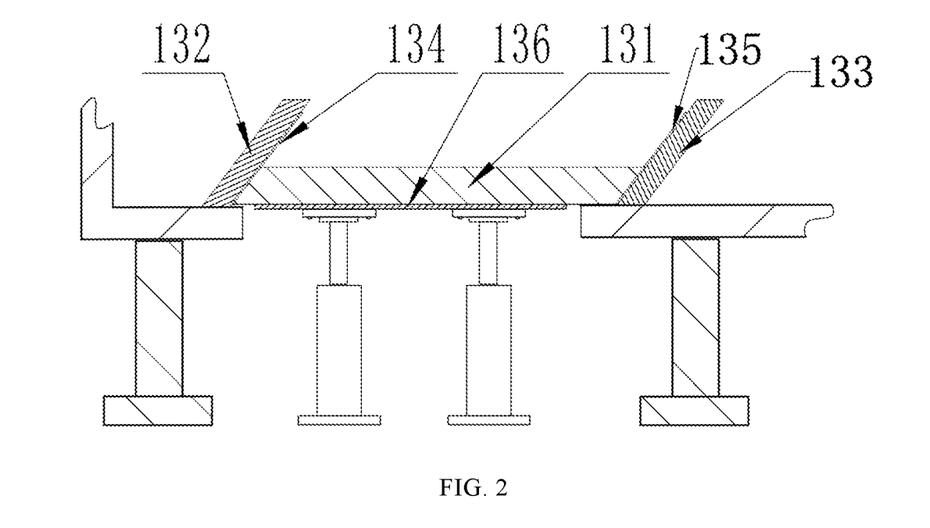
FIG. 2 is a schematic view of a plate assembly shown in FIG. 1.
Figure 3:
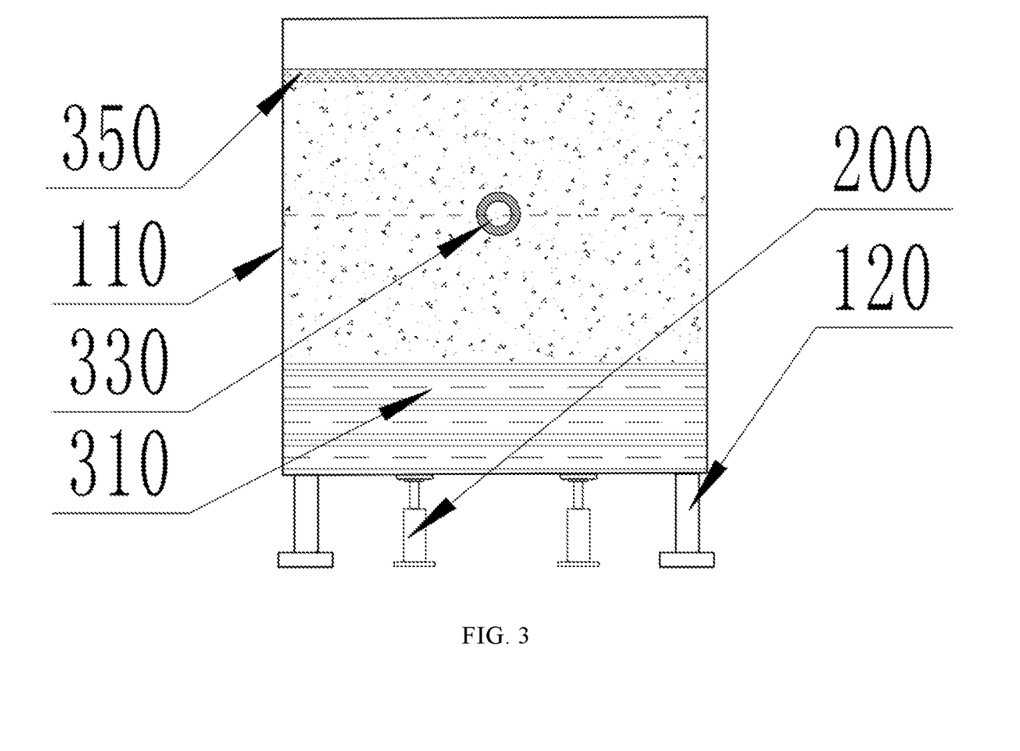
FIG. 3 is a schematic view of the structure shown in FIG. 1 from another angle.

Referring to FIGS. 1 to 3, the present invention provides an experimental system for simulating creep and stick-slip dislocations of a fault in a tunnel structure. The experimental system includes a model box system and a fault dislocation loading system. The fault dislocation loading system is provided under the model box system. The model box system includes a hollow box structure 110 and a supporting device 120 provided under the box structure. The hollow and open box structure provides a space for the materials similar to the surrounding rock and the tunnel structure model.

Further, a friction effect layer 310, a first surrounding rock layer 320, a tunnel structure model 330, a second surrounding rock layer 340 and an overburden pressure layer 350 are sequentially arranged in the box structure from bottom to top. A bottom of the box structure is provided with a through hole. A plate assembly is provided on the through hole to close the bottom of the box structure. In this embodiment, the friction effect layer, the first surrounding rock layer, the second surrounding rock layer and the overburden pressure layer materials similar to a surrounding rock to truly simulate the environment of a tunnel.

The plate assembly includes a loading plate 131, a first guide plate 132 and a second guide plate 133. The loading plate covers the through hole. The first guide plate and the second guide plate are arranged on two sides of the loading plate and are connected to a bottom plate of the box structure. A side of the first guide plate adjacent to the second guide plate is provided with a first slide rail 134, and a side of the second guide plate adjacent to the first guide plate is provided with a second slide rail 135. The two sides of the loading plate are slidably provided on the first slide rail and the second slide rail. The fault dislocation loading system 200 is provided under the loading plate. The loading plate moves along the first slide rail and the second slide rail under the action of the fault dislocation loading system. The friction effect layer provides fault dislocation power to the tunnel structure model through the first surrounding rock layer under the action of the loading plate to simulate fault dislocation effects.

Preferably, the first guide plate and the second guide plate are inclined plates; two side end surfaces of the loading plate are inclined surfaces, and the first guide plate and the second guide plate are arranged in parallel with the two side end surfaces of the loading plate. The first guide plate and the second guide plate are detachably arranged at the bottom of the box structure, and their inclination can be flexibly adjusted. Through the inclined first guide plate and second guide plate, the loading plate moves obliquely upwards at certain angles to simulate specific dislocation angles, so as to carry out simulations under different fault dislocation angles, which improves the accuracy of the experiment.

Further, a third slide rail 136 is provided at a bottom of the loading plate; the fault dislocation loading system includes a plurality of hydraulic power devices; tops of the plurality of hydraulic power devices abut against the third slide rail during an experiment, and tops of the plurality of hydraulic power devices are slidable on the third slide rail.

In this embodiment, the hydraulic power device includes a jack. A base of the jack is fixedly connected to a ground, and a piston rod of the jack is in contact with the loading plate to serve as a source of loading power for the experiment.

Further, the friction effect layer includes clay mineral and quartz sand, and each of the first surrounding rock layer and the second surrounding rock layer is a mixture of quartz sand, barite powder, gypsum and water. These components are used to simulate the surrounding rock of the tunnel, and their ratio is calculated through a similarity theory based on the surrounding rock environment of the prototype tunnel. The tunnel structure is buried in the middle of the surrounding rock. The clay mineral is kaolinite, illite or montmorillonite, etc.

Preferably, the tunnel structure model is provided between the first surrounding rock layer and the second surrounding rock layer.

Preferably, in a process of simulating a creep, a weight ratio of the clay mineral to the quartz sand is 1:1, the clay mineral is montmorillonite, and the quartz sand is 80-mesh ordinary quartz sand.

Preferably, in a process of simulating a stick-slip, the weight ratio of the clay mineral to the quartz sand is 1:9, the clay mineral is kaolinite, and the quartz sand is 40-mesh ordinary quartz sand.

Preferably, a height of the first guide plate and a height of the second guide plate are less than a height of the friction effect layer.

Further, an angle between the first guide plate and the bottom plate of the box structure is θ, where $\theta \in [15°, 90°]$.

Further, the height of the friction effect layer is h, and a height of the box structure is H, $h \in [\frac{1}{3}H, \frac{1}{2}H]$.

Preferably, the overburden pressure layer is an iron sand layer covering an outermost layer as a counterweight material to provide an overburden pressure to simulate stress from a buried depth of an overlying layer that a tunnel with a large-buried depth bears.

Further, the supporting device includes a plurality of supporting frames, and the plurality of supporting frames are arranged in an array; the supporting frame has a T-shaped structure, and the top of the T-shaped structure is detachably connected to the bottom of the box structure.

Preferably, the supporting frames are steel supporting legs, which are fixedly connected to the ground to ensure the stability of the box during the experiment.

Further, the bottom plate of the box structure includes a first region and a second region, and the first region and the second region are symmetrically arranged; and the through hole is provided at the first region or the second region. In this embodiment, the through hole is provided in a left or right half of the bottom plate of the box structure. In this embodiment, the through hole is a square hole provided in a left half of the bottom of the box structure, which has an area less than that of the loading plate.

Preferably, a front panel, a rear panel, a left panel and a right panel of the box structure are made of organic glass. They are convenient for real-time observation of the deformation and damage of the tunnel structure and the surrounding rock during the experiment.

Further, the experimental system further includes a master control center, a deformation detection device and a high-energy accelerator-based CT scanning system; the deformation detection device and the high-energy accelerator-based CT scanning system are connected to the master control center through signals; the deformation detection device includes a first deformation detection assembly, a second deformation detection assembly, a third deformation detection assembly and a fourth deformation detection assembly; and the first deformation detection assembly is provided in the friction effect layer to detect deformation of the friction effect layer in real time; the second deformation detection assembly is provided in the first surrounding rock layer to detect deformation of the first surrounding rock layer in real time; the third deformation detection assembly is provided in the tunnel structure model to detect deformation of a peripheral side wall of the tunnel structure model in real time; the fourth deformation detection assembly is provided in the second surrounding rock layer to detect deformation of the second surrounding rock layer in real time; the high-energy accelerator-based CT scanning system includes a ray source device and a detector; and the ray source device and the detector are respectively arranged on two sides of the tunnel structure model in the box structure for real-time detection of stress and deformation states of the rock surrounding the tunnel structure model and a tunnel structure.

Further, in this embodiment, the tunnel structure model is a long cylindrical gypsum model, a cross-section of which may be round or horseshoe-shaped according to the simulated tunnel; and a strain gauge and a micro-camera, etc. may be set up as needed to implement real-time deformation measurement, dynamic rupture shooting and other experimental detection means.

To realize the experimental simulations of creep and stick-slip dislocations, this system only needs to change the composition and proportion of the clay mineral in the friction effect layer made of materials similar to the surrounding rock. The influence of the fault dislocation on the tunnel studied in the experiment is implemented by transferring the relative motion of the rock mass on both sides of the fault to the overlying rock and soil to produce deformation and damage to the buried tunnel structure. The essence of the fault dislocation is the shear dislocation of the rock mass discontinuities, which involves the constitutive relationship of discontinuity shear. Discontinuity shear is dependent on the contact time, speed and displacement, which determines the stability (creep) or instability (stick-slip) of frictional slip.

The Dieterich-Ruina law (or slowness law) that expresses the shear constitutive relationship of the rock mass discontinuities is: $\tau=[\mu_0+a \ln(V/V_0)+b \ln(V_0\theta/L)]\bar{\sigma}$. $\tau$ is an effective shear force, $\bar{\sigma}$ is an effective normal stress, V is a slip speed, $V_0$ is a reference speed, $\mu_0$ is a steady-state friction coefficient, a and b are parameters that characterize material properties, and L is a critical slip distance.

The main parameter that determines the friction stability is a-b. When conforming to a-b≥0, the material is speed-enhanced and maintains stable slip (creep). When conforming to a-b<0, the material is speed-weakened and presents unstable slip (stick-slip). Shear experiments on the rock mass discontinuities have shown that when the weight percentage of the clay mineral is greater than 30%, the slip receives a speed-enhancing effect, which appears as a creep. When the weight percentage of the clay mineral is less than 30%, the slip receives a speed-weakening effect, which appears as a stick-slip. Therefore, the present invention considers the influence of the proportion of the clay mineral in the friction effect layer made of similar materials to the surrounding rock on the friction stability. In a process of simulating creep, the weight ratio of the clay mineral to the quartz sand in the friction effect layer is preferably 50%: 50%, the clay mineral is montmorillonite, and the quartz sand is 80-mesh ordinary quartz sand. In a process of simulating stick-slip, the weight ratio of the clay mineral to the quartz sand in the friction effect layer is 10%:90%, the clay mineral is kaolinite, and the quartz sand is 40-mesh ordinary quartz sand.

In addition, an appropriate amount of barite powder may be added to fine-tune the friction coefficient and friction effect.

A specific experimental method of this experimental system is as follows. 1) The experimental device is assembled and adjusted according to experimental requirements. The loading plate is provided on the square hole (i.e. through hole) of the bottom plate of the box structure. The four sides of the loading plate do not contact the side walls of the box structure to avoid friction. A loading jack group (i.e. the fault dislocation loading system) is adjusted such that the piston rods of the jacks are in close contact with the third slide rail at the bottom of the loading plate. The fixing bolts of the inclined guide plates are loosened to adjust the inclination of the guide plates to be equal to that of the fault dislocation to be simulated, and then the fixing bolts are tightened.

2) The tunnel structure model is fabricated. Gypsum is used to make the tunnel structure and its internal lining model. The cross-sectional shape of the model is consistent with that of the simulated tunnel. According to the experimental requirements, lining and rail system models may also be made in the tunnel, and monitoring equipment such as a strain gauge and a micro camera may also be arranged.

3) The materials similar to the surrounding rock are loaded. According to the fault dislocation (i.e. creep or stick-slip) to be simulated in the experiment, the ratio of the similar materials of the corresponding friction layer is selected. The materials are well mixed according to the ratio and laid multiple times on the bottom of the box structure, with a height not exceeding ⅓ of the inner height of the box structure. The proportion of the similar materials in the surrounding rock layers is determined through a similarity theory or other method. The materials are mixed well according to the ratio. Then, half of the materials are laid multiple times on the friction effect layer to form the first surrounding rock layer. The tunnel structure model is placed, and monitoring equipment such as the strain gauge and an earth pressure cell are arranged according to specific requirements. The remaining materials are laid multiple times to cover the tunnel structure and serve as the second surrounding rock layer. A layer of iron sand is spread on the surface according to a simulated buried depth to increase the overburden pressure, and the amount of iron sand is calculated according to the simulated overburden pressure.

4) Experiment loading and monitoring. The loading jack group pushes the loading plate upward. The friction effect layer generates a friction dislocation under the action of the loading plate, produces a creep or stick-slip under different contents of the clay mineral, and further transfers the dislocation effect to the first surrounding rock layer and the second surrounding rock layer. Under the dislocation, the first surrounding rock layer, the second surrounding rock layer and the tunnel structure model interact, and deform and fail, so as to simulate the influence of the fault dislocation on the tunnel structure. During the experiment, the surrounding rock deformation can be observed in real time through the organic glass panels of the model box, and the experimental data can be acquired through the monitoring equipment such as the strain gauge, the micro-camera and the soil pressure cell.

5) End of the experiment. When the displacement of the loading plate reaches a preset displacement amount, the loading is stopped. The overlying materials are removed layer by layer, and the tunnel structure model is taken out. Finally, the loading jack group and the loading plate are reset to end the experiment.

Although the present invention has been described with reference to the preferred embodiments, various improvements can be made and components therein can be replaced with equivalents without departing from the scope of the present invention. In particular, as long as there is no structural conflict, the technical features in the embodiments can be combined in any way. The present invention is not limited to the specific embodiments disclosed herein, but should include all technical solutions falling within the scope of the claims.

In the description of the present invention, terms such as "central", "upper", "lower", "left", "right", "vertical", "horizontal", "inner", and "outer" indicate orientation or position relationships based on the drawings. They are merely intended to facilitate description, rather than to indicate or imply that the mentioned apparatus or components must have the specific orientation and must be constructed and operated in the specific orientation. Therefore, these terms should not be construed as a limitation to the present invention. Moreover, the terms "first", "second" and "third" are used only for the purpose of description, rather than to indicate or imply relative importance.

In addition, it should be noted that in the description of the present invention, unless otherwise clearly specified, meanings of terms "install", "connect with" and "connect to" should be understood in a broad sense. For example, the connection may be a fixed connection, a removable connection, or an integral connection, may be a mechanical connection or an electrical connection, may be a direct connection or an indirect connection via a medium, and may be an internal connection between two components. Those skilled in the art should understand the specific meanings of the above terms in the present invention based on specific situations.

In addition, terms "include", "comprise", or any other variations thereof are intended to cover non-exclusive inclusions, so that a process, an article, or a device/apparatus including a series of elements not only includes those elements, but also includes other elements that are not explicitly listed, or also includes inherent elements of the process, the article or the device/apparatus.

The technical solutions of the present invention are described with reference to the preferred implementations and drawings. Those skilled in the art should easily understand that the protection scope of the present invention is apparently not limited to these specific implementations. Those skilled in the art can make equivalent changes or substitutions to the relevant technical features without departing from the principles of the present invention, and the technical solutions derived by making these changes or substitutions should fall within the protection scope of the present invention.

What is claimed is:

1. An experimental system for simulating creep and stick-slip dislocations of a fault in a tunnel structure, comprising a model box system and a fault dislocation loading system, wherein the fault dislocation loading system is provided under the model box system;
   the model box system comprises a box structure being hollow and a supporting device provided under the box structure; wherein
   a friction effect layer, a first surrounding rock layer, a tunnel structure model, a second surrounding rock layer and an overburden pressure layer are sequentially arranged in the box structure from bottom to top;
   a bottom of the box structure is provided with a through hole;
   a plate assembly is provided on the through hole to close the bottom of the box structure;
   the friction effect layer comprises clay mineral and quartz sand; and
   each of the first surrounding rock layer and the second surrounding rock layer is a mixture of quartz sand, barite powder, gypsum and water;
   in a process of simulating a creep, a weight ratio of the clay mineral to the quartz sand is 1:1, the clay mineral is montmorillonite, and the quartz sand is 80-mesh ordinary quartz sand;
   in a process of simulating a stick-slip, the weight ratio of the clay mineral to the quartz sand is 1:9, the clay mineral is kaolinite, and the quartz sand is 40-mesh ordinary quartz sand;
   the plate assembly comprises a loading plate, a first guide plate and a second guide plate; wherein
   the loading plate covers the through hole;
   the first guide plate and the second guide plate are arranged on two sides of the loading plate, and the first guide plate and the second guide plate are connected to a bottom plate of the box structure;
   a side of the first guide plate is provided with a first slide rail, wherein the side of the first guide plate is adjacent to the second guide plate;
   a side of the second guide plate is provided with a second slide rail, wherein the side of the second guide plate is adjacent to the first guide plate; and
   the two sides of the loading plate are slidably provided on the first slide rail and the second slide rail;
   the fault dislocation loading system is provided under the loading plate;
   the loading plate moves along the first slide rail and the second slide rail under an action of the fault dislocation loading system; and
   the friction effect layer provides fault dislocation power to the tunnel structure model through the first surrounding rock layer under an action of the loading plate.

2. The experimental system according to claim 1, wherein the first guide plate and the second guide plate are inclined plates;
   two side end surfaces of the loading plate are inclined surfaces;
   the first guide plate and the second guide plate are arranged in parallel with the two side end surfaces of the loading plate;
   a third slide rail is provided at a bottom of the loading plate; and
   the fault dislocation loading system comprises a plurality of hydraulic power devices wherein tops of the plurality of hydraulic power devices abut against the third slide rail during an experiment, and tops of the plurality of hydraulic power devices are slidable on the third slide rail.

3. The experimental system according to claim 1, wherein the tunnel structure model is provided between the first surrounding rock layer and the second surrounding rock layer.

4. The experimental system according to claim 2, wherein a height of the first guide plate and a height of the second guide plate are less than a height of the friction effect layer; and
   an angle between the first guide plate and the bottom plate of the box structure is θ, wherein θ∈[15°, 90°].

5. The experimental system according to claim 4, wherein the height of the friction effect layer is h, and a height of the box structure is H, wherein $$h \in \left[\frac{1}{3}H, \frac{1}{2}H\right].$$

6. The experimental system according to claim 1, wherein
the overburden pressure layer is an iron sand layer;
the supporting device comprises a plurality of supporting frames, and the plurality of supporting frames are arranged in an array; and
each of the plurality of supporting frames has a T-shaped structure, and a top of the T-shaped structure is detachably connected to the bottom of the box structure.

7. The experimental system according to claim 6, wherein
the bottom plate of the box structure comprises a first region and a second region, and the first region and the second region are symmetrically arranged;
the through hole is provided at the first region or the second region; and
a front panel, a rear panel, a left panel and a right panel of the box structure are made of organic glass.

8. The experimental system according to claim 1, further comprising a master control center, a deformation detection device and a high-energy accelerator-based computed tomography (CT) scanning system; wherein
the deformation detection device and the high-energy accelerator-based CT scanning system are connected to the master control center through signals; and
the deformation detection device comprises a first deformation detection assembly, a second deformation detection assembly, a third deformation detection assembly and a fourth deformation detection assembly; wherein
the first deformation detection assembly is provided in the friction effect layer to detect deformation of the friction effect layer in real time;
the second deformation detection assembly is provided in the first surrounding rock layer to detect deformation of the first surrounding rock layer in real time;
the third deformation detection assembly is provided in the tunnel structure model to detect deformation of a peripheral side wall of the tunnel structure model in real time;
the fourth deformation detection assembly is provided in the second surrounding rock layer to detect deformation of the second surrounding rock layer in real time; and
the high-energy accelerator-based CT scanning system comprises a ray source device and a detector, wherein the ray source device and the detector are respectively arranged on two sides of the tunnel structure model in the box structure for real-time detection of stress and deformation states of rock surrounding the tunnel structure model.

9. The experimental system according to claim 2, further comprising a master control center, a deformation detection device and a high-energy accelerator-based computed tomography (CT) scanning system; wherein
the deformation detection device and the high-energy accelerator-based CT scanning system are connected to the master control center through signals; and
the deformation detection device comprises a first deformation detection assembly, a second deformation detection assembly, a third deformation detection assembly and a fourth deformation detection assembly; wherein
the first deformation detection assembly is provided in the friction effect layer to detect deformation of the friction effect layer in real time;
the second deformation detection assembly is provided in the first surrounding rock layer to detect deformation of the first surrounding rock layer in real time;
the third deformation detection assembly is provided in the tunnel structure model to detect deformation of a peripheral side wall of the tunnel structure model in real time;
the fourth deformation detection assembly is provided in the second surrounding rock layer to detect deformation of the second surrounding rock layer in real time; and
the high-energy accelerator-based CT scanning system comprises a ray source device and a detector, wherein the ray source device and the detector are respectively arranged on two sides of the tunnel structure model in the box structure for real-time detection of stress and deformation states of rock surrounding the tunnel structure model.

10. The experimental system according to claim 3, further comprising a master control center, a deformation detection device and a high-energy accelerator-based computed tomography (CT) scanning system; wherein
the deformation detection device and the high-energy accelerator-based CT scanning system are connected to the master control center through signals; and
the deformation detection device comprises a first deformation detection assembly, a second deformation detection assembly, a third deformation detection assembly and a fourth deformation detection assembly; wherein
the first deformation detection assembly is provided in the friction effect layer to detect deformation of the friction effect layer in real time;
the second deformation detection assembly is provided in the first surrounding rock layer to detect deformation of the first surrounding rock layer in real time;
the third deformation detection assembly is provided in the tunnel structure model to detect deformation of a peripheral side wall of the tunnel structure model in real time;
the fourth deformation detection assembly is provided in the second surrounding rock layer to detect deformation of the second surrounding rock layer in real time; and
the high-energy accelerator-based CT scanning system comprises a ray source device and a detector, wherein the ray source device and the detector are respectively arranged on two sides of the tunnel structure model in the box structure for real-time detection of stress and deformation states of rock surrounding the tunnel structure model.

11. The experimental system according to claim 4, further comprising a master control center, a deformation detection device and a high-energy accelerator-based computed tomography (CT) scanning system; wherein
the deformation detection device and the high-energy accelerator-based CT scanning system are connected to the master control center through signals; and
the deformation detection device comprises a first deformation detection assembly, a second deformation detection assembly, a third deformation detection assembly and a fourth deformation detection assembly; wherein
the first deformation detection assembly is provided in the friction effect layer to detect deformation of the friction effect layer in real time;
the second deformation detection assembly is provided in the first surrounding rock layer to detect deformation of the first surrounding rock layer in real time;

the third deformation detection assembly is provided in the tunnel structure model to detect deformation of a peripheral side wall of the tunnel structure model in real time;

the fourth deformation detection assembly is provided in the second surrounding rock layer to detect deformation of the second surrounding rock layer in real time; and the high-energy accelerator-based CT scanning system comprises a ray source device and a detector, wherein the ray source device and the detector are respectively arranged on two sides of the tunnel structure model in the box structure for real-time detection of stress and deformation states of rock surrounding the tunnel structure model.

12. The experimental system according to claim 5, further comprising a master control center, a deformation detection device and a high-energy accelerator-based computed tomography (CT) scanning system; wherein the deformation detection device and the high-energy accelerator-based CT scanning system are connected to the master control center through signals; and the deformation detection device comprises a first deformation detection assembly, a second deformation detection assembly, a third deformation detection assembly and a fourth deformation detection assembly; wherein the first deformation detection assembly is provided in the friction effect layer to detect deformation of the friction effect layer in real time;

the second deformation detection assembly is provided in the first surrounding rock layer to detect deformation of the first surrounding rock layer in real time;

the third deformation detection assembly is provided in the tunnel structure model to detect deformation of a peripheral side wall of the tunnel structure model in real time;

the fourth deformation detection assembly is provided in the second surrounding rock layer to detect deformation of the second surrounding rock layer in real time; and the high-energy accelerator-based CT scanning system comprises a ray source device and a detector, wherein the ray source device and the detector are respectively arranged on two sides of the tunnel structure model in the box structure for real-time detection of stress and deformation states of rock surrounding the tunnel structure model.

13. The experimental system according to claim 6, further comprising a master control center, a deformation detection device and a high-energy accelerator-based computed tomography (CT) scanning system; wherein the deformation detection device and the high-energy accelerator-based CT scanning system are connected to the master control center through signals; and the deformation detection device comprises a first deformation detection assembly, a second deformation detection assembly, a third deformation detection assembly and a fourth deformation detection assembly; wherein the first deformation detection assembly is provided in the friction effect layer to detect deformation of the friction effect layer in real time;

the second deformation detection assembly is provided in the first surrounding rock layer to detect deformation of the first surrounding rock layer in real time;

the third deformation detection assembly is provided in the tunnel structure model to detect deformation of a peripheral side wall of the tunnel structure model in real time;

the fourth deformation detection assembly is provided in the second surrounding rock layer to detect deformation of the second surrounding rock layer in real time; and the high-energy accelerator-based CT scanning system comprises a ray source device and a detector, wherein the ray source device and the detector are respectively arranged on two sides of the tunnel structure model in the box structure for real-time detection of stress and deformation states of rock surrounding the tunnel structure model.

14. The experimental system according to claim 7, further comprising a master control center, a deformation detection device and a high-energy accelerator-based computed tomography (CT) scanning system; wherein the deformation detection device and the high-energy accelerator-based CT scanning system are connected to the master control center through signals; and the deformation detection device comprises a first deformation detection assembly, a second deformation detection assembly, a third deformation detection assembly and a fourth deformation detection assembly; wherein the first deformation detection assembly is provided in the friction effect layer to detect deformation of the friction effect layer in real time;

the second deformation detection assembly is provided in the first surrounding rock layer to detect deformation of the first surrounding rock layer in real time;

the third deformation detection assembly is provided in the tunnel structure model to detect deformation of a peripheral side wall of the tunnel structure model in real time;

the fourth deformation detection assembly is provided in the second surrounding rock layer to detect deformation of the second surrounding rock layer in real time; and the high-energy accelerator-based CT scanning system comprises a ray source device and a detector, wherein the ray source device and the detector are respectively arranged on two sides of the tunnel structure model in the box structure for real-time detection of stress and deformation states of rock surrounding the tunnel structure model.

\* \* \* \* \*